United States Patent
Sullivan

(10) Patent No.: US 11,938,334 B2
(45) Date of Patent: Mar. 26, 2024

(54) WEARABLE CARDIOVERTER DEFIBRILLATOR (WCD) SYSTEM CHOOSING TO CONSIDER ECG SIGNALS FROM DIFFERENT CHANNELS PER QRS COMPLEX WIDTHS OF THE ECG SIGNALS

(71) Applicant: West Affum Holdings DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

(21) Appl. No.: 17/960,436

(22) Filed: Oct. 5, 2022

(65) Prior Publication Data

US 2023/0023203 A1    Jan. 26, 2023

Related U.S. Application Data

(60) Continuation of application No. 16/366,313, filed on Mar. 27, 2019, now Pat. No. 11,471,693, which is a
(Continued)

(51) Int. Cl.
*A61N 1/39* (2006.01)
*A61B 5/0245* (2006.01)
(Continued)

(52) U.S. Cl.
CPC .......... *A61N 1/3987* (2013.01); *A61B 5/0245* (2013.01); *A61N 1/025* (2013.01);
(Continued)

(58) Field of Classification Search
CPC ...... A61N 1/3987; A61N 1/025; A61N 1/046; A61N 1/3904; A61N 1/3925; A61N 1/0484; A61B 5/0245; A61B 5/7275
See application file for complete search history.

(56) References Cited

U.S. PATENT DOCUMENTS

| | | |
|---|---|---|
| 3,724,455 A | 4/1973 | Unger |
| 4,291,699 A | 9/1981 | Geddes et al. |

(Continued)

FOREIGN PATENT DOCUMENTS

| | | |
|---|---|---|
| CA | 2942933 A1 | 8/2015 |
| CN | 103405851 A | 11/2013 |
| WO | 9839061 A2 | 9/1998 |

OTHER PUBLICATIONS

U.S. Appl. No. 62/630,398, filed Feb. 14, 2018, Sullivan.
(Continued)

*Primary Examiner* — Catherine M Voorhees
(74) *Attorney, Agent, or Firm* — Spectrum IP Law Group LLC

(57) ABSTRACT

In embodiments, a wearable cardioverter defibrillator (WCD) system includes a support structure for wearing by an ambulatory patient. When worn, the support structure maintains electrodes on the patient's body. Different pairs of these electrodes define different channels, and different patient ECG signals can be sensed from the channels. The ECG signals can be analyzed to determine which one is the best to use, for the WCD system to make a shock/no shock decision. The analysis can be according to widths of the QRS complexes, consistency of the QRS complexes, or heart rate agreement statistics.

16 Claims, 15 Drawing Sheets

COMPONENTS OF
SAMPLE WCD SYSTEM

Related U.S. Application Data division of application No. 16/268,870, filed on Feb. 6, 2019, now abandoned.

(60) Provisional application No. 62/660,822, filed on Apr. 20, 2018, provisional application No. 62/630,398, filed on Feb. 14, 2018.

(51) Int. Cl.
*A61N 1/02* (2006.01)
*A61N 1/04* (2006.01)

(52) U.S. Cl.
CPC ........... *A61N 1/046* (2013.01); *A61N 1/3904* (2017.08); *A61N 1/3925* (2013.01); *A61N 1/0484* (2013.01)

(56) References Cited

U.S. PATENT DOCUMENTS

| | | |
|---|---|---|
| 4,583,524 A | 4/1986 | Hutchins |
| 4,617,938 A | 10/1986 | Shimoni et al. |
| 4,619,265 A | 10/1986 | Morgan et al. |
| 4,895,151 A | 1/1990 | Grevis et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,376,104 A | 12/1994 | Sakai et al. |
| 5,381,803 A | 1/1995 | Herleikson et al. |
| 5,394,892 A | 3/1995 | Kenny et al. |
| 5,405,362 A | 4/1995 | Kramer et al. |
| 5,425,749 A | 6/1995 | Adams |
| 5,474,574 A | 12/1995 | Payne et al. |
| 5,554,174 A | 9/1996 | Causey, III |
| 5,601,612 A | 2/1997 | Gliner et al. |
| 5,630,834 A | 5/1997 | Bardy |
| 5,662,690 A | 9/1997 | Cole et al. |
| 5,709,215 A | 1/1998 | Perttu et al. |
| 5,769,872 A | 6/1998 | Lopin et al. |
| 5,782,878 A | 7/1998 | Morgan et al. |
| 5,792,204 A | 8/1998 | Snell |
| 5,803,927 A | 9/1998 | Cameron et al. |
| 5,819,007 A | 10/1998 | Elghazzawi |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,068,651 A | 5/2000 | Brandell |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,427,083 B1 | 7/2002 | Owen et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,694,187 B1 | 2/2004 | Freeman |
| 6,762,917 B1 | 7/2004 | Verbiest et al. |
| 6,941,168 B2 | 9/2005 | Girouard |
| 7,065,401 B2 | 6/2006 | Worden |
| 7,149,576 B1 | 12/2006 | Baura et al. |
| 7,336,994 B2 | 2/2008 | Hettrick et al. |
| 7,379,771 B2 | 5/2008 | Kovac et al. |
| 7,460,900 B1 | 12/2008 | Gill et al. |
| 7,559,902 B2 | 7/2009 | Ting et al. |
| 7,865,238 B2 | 1/2011 | Brink |
| 7,870,761 B2 | 1/2011 | Valentine et al. |
| 7,894,894 B2 | 2/2011 | Stadler et al. |
| 7,974,689 B2 | 7/2011 | Volpe et al. |
| 8,024,037 B2 | 9/2011 | Kumar |
| 8,036,746 B2 | 10/2011 | Sanders |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,825,154 B2 | 9/2014 | Jorgenson et al. |
| 8,838,235 B2 | 9/2014 | Cowan et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 8,996,101 B2 | 3/2015 | Zhang et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,533,165 B1 | 1/2017 | Gunderson |
| 9,592,403 B2 * | 3/2017 | Sullivan ............... A61N 1/3925 |
| 9,757,579 B2 | 9/2017 | Foshee, Jr. et al. |
| 9,757,581 B2 | 9/2017 | Sullivan et al. |
| 10,016,614 B2 | 7/2018 | Sullivan |
| 10,322,291 B2 | 6/2019 | Medema et al. |
| 11,160,990 B1 | 11/2021 | Sullivan et al. |
| 11,331,508 B1 | 5/2022 | Cowan et al. |
| 2011/0022105 A9 | 1/2003 | Owen et al. |
| 2003/0158593 A1 | 8/2003 | Heilman et al. |
| 2003/0187479 A1 | 10/2003 | Thong |
| 2004/0049117 A1 | 3/2004 | Ideker et al. |
| 2004/0220623 A1 | 11/2004 | Hess |
| 2004/0230105 A1 | 11/2004 | Geva et al. |
| 2005/0107833 A1 | 5/2005 | Freeman et al. |
| 2005/0107834 A1 | 5/2005 | Freeman et al. |
| 2005/0131476 A1 | 6/2005 | Kim et al. |
| 2006/0017575 A1 | 1/2006 | McAdams |
| 2006/0173364 A1 | 8/2006 | Clancy et al. |
| 2007/0179539 A1 | 8/2007 | DeGroot et al. |
| 2007/0203418 A1 | 8/2007 | Starc |
| 2008/0208070 A1 | 8/2008 | Snyder et al. |
| 2008/0215103 A1 | 9/2008 | Powers et al. |
| 2008/0306560 A1 | 12/2008 | Macho et al. |
| 2008/0312708 A1 | 12/2008 | Snyder |
| 2008/0312709 A1 | 12/2008 | Volpe et al. |
| 2009/0005827 A1 | 1/2009 | Weintraub et al. |
| 2009/0018595 A1 | 1/2009 | Bharmi et al. |
| 2010/0007413 A1 | 1/2010 | Herleikson et al. |
| 2010/0114248 A1 | 5/2010 | Donofrio et al. |
| 2010/0298899 A1 | 11/2010 | Donnelly et al. |
| 2010/0331904 A1 | 12/2010 | Warren et al. |
| 2011/0288604 A1 | 11/2011 | Kaib et al. |
| 2011/0288605 A1 | 11/2011 | Kaib et al. |
| 2012/0022355 A1 | 1/2012 | Byrd et al. |
| 2012/0150008 A1 | 1/2012 | Lanar et al. |
| 2012/0059270 A1 | 3/2012 | Grunwald |
| 2012/0108911 A1 | 5/2012 | Drysdale et al. |
| 2012/0112903 A1 | 5/2012 | Kaib et al. |
| 2012/0144551 A1 | 6/2012 | Guldalian |
| 2012/0158075 A1 | 6/2012 | Kaib et al. |
| 2012/0265265 A1 | 10/2012 | Razavi et al. |
| 2012/0277638 A1 | 11/2012 | Skelton et al. |
| 2012/0283794 A1 | 11/2012 | Kaib et al. |
| 2012/0293323 A1 | 11/2012 | Kaib et al. |
| 2012/0302860 A1 * | 11/2012 | Volpe ..................... A61B 5/341 |
| | | 600/512 |
| 2012/0310315 A1 | 12/2012 | Savage et al. |
| 2012/0316611 A1 | 12/2012 | Armoundas et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |

(56) References Cited

U.S. PATENT DOCUMENTS

| | | |
|---|---|---|
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinotti-Buitoni et al. |
| 2014/0081162 A1 | 3/2014 | Snell et al. |
| 2014/0150781 A1 | 6/2014 | Capua et al. |
| 2014/0163395 A1 | 6/2014 | Sapp, Jr. et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0037636 A1 | 2/2015 | Amsler et al. |
| 2015/0039053 A1 | 2/2015 | Kaib et al. |
| 2015/0105835 A1 | 4/2015 | Thakur et al. |
| 2015/0265845 A1 | 9/2015 | Sullivan et al. |
| 2015/0297107 A1 | 10/2015 | Sullivan et al. |
| 2015/0328472 A1 | 11/2015 | Sullivan et al. |
| 2016/0000349 A1 | 1/2016 | Sullivan et al. |
| 2016/0004831 A1 | 1/2016 | Carlson et al. |
| 2016/0007877 A1 | 1/2016 | Felix et al. |
| 2016/0015329 A1 | 1/2016 | Kohlrausch et al. |
| 2016/0067514 A1 | 3/2016 | Sullivan |
| 2016/0074667 A1 | 3/2016 | Sullivan et al. |
| 2016/0082277 A1 | 3/2016 | Foshee, Jr. et al. |
| 2016/0106332 A1 | 4/2016 | Takeshima |
| 2016/0121100 A1 | 5/2016 | Crone et al. |
| 2016/0235320 A1 | 8/2016 | Sarkar et al. |
| 2016/0278698 A1 | 9/2016 | Freeman et al. |
| 2016/0331984 A1 | 11/2016 | Firoozabadi et al. |
| 2016/0353996 A1 | 12/2016 | Fink |
| 2017/0056682 A1 | 3/2017 | Kumar et al. |
| 2017/0157416 A1 | 6/2017 | Medema et al. |
| 2017/0252571 A1 | 9/2017 | Dascoli et al. |
| 2018/0028083 A1 | 2/2018 | Greenhut et al. |
| 2018/0093102 A1 | 4/2018 | Sullivan et al. |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0221648 A1 | 8/2018 | Gustavson et al. |
| 2018/0264279 A1 | 9/2018 | Kim et al. |
| 2018/0318593 A1 | 11/2018 | Sullivan |
| 2019/0030351 A1 | 1/2019 | Sullivan et al. |
| 2019/0030352 A1 | 1/2019 | Sullivan et al. |
| 2020/0164217 A1 | 5/2020 | Sullivan |
| 2022/0032077 A1 | 2/2022 | Sullivan et al. |

OTHER PUBLICATIONS

Duncker et al. "Real-world Experience of 355 Consecutive Patients with a Wearable Cardioverter/Debrillator—Single Centre Analysis" Europace 2017, No. 19 Supplemental 3, iii304.

EPO Search Report dated Dec. 19, 2018 on EP Application No. 1816221.0-1224.

EPO Search report dated Sep. 27, 2018 on EP Application 18186229.3-1224.

European Search Report of European Application 16202067.1-1666, dated Apr. 25, 2017.

First Office action and Search Report dated Aug. 30, 2018, to CN Patent Application No. 2016111063501.

Heartstart MRx and XL AED Algorithm—Application Note, Jul. 2001, Edition 2 Philips Healthcare, USA.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Olgin JE, Pletcher MJ, Vittinghoff E, et al., "Wearable Cardioverter-Defibrillator after Myocardial Infarction," N Engl J Med Sep. 27, 2018; 379(13):1205-1215.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Schuhmann et al., "Experience with the wearable cardioverter defibrillator (WCD) in high risk cardiac patients from a German single center cohort", Heart Rhythm 2016;13(5):S254.

Second Office Action dated May 18, 2020, to CN Patent Application No. 2016111106350.1.

The LifeVest Network/Patient Data Management System, Zoll, 2015, 2000503 Rev A.

WCD Performance for Clinical Review, Sullivan et al., "A Novel Wearable Cardioverter Defibrillator With Reduced False Alarm Rate," AHA 2017.

\* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

COMPONENTS OF SAMPLE WCD SYSTEM

MULTIPLE ELECTRODES FOR
SENSING ECG SIGNALS ALONG
DIFFERENT VECTORS

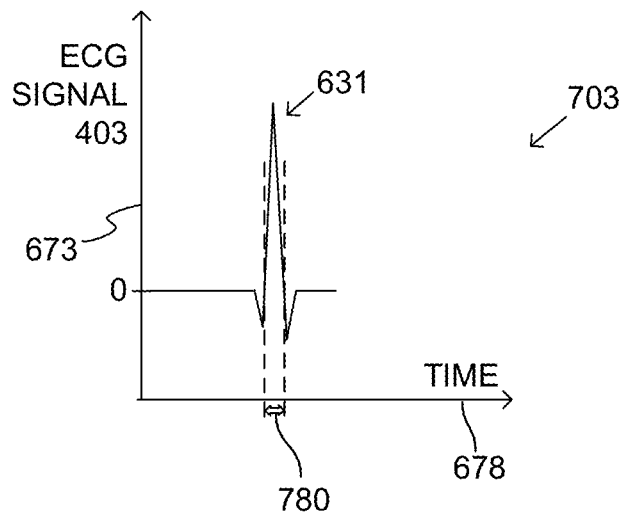
FIG. 7  *QRS WIDTH – GENERIC*
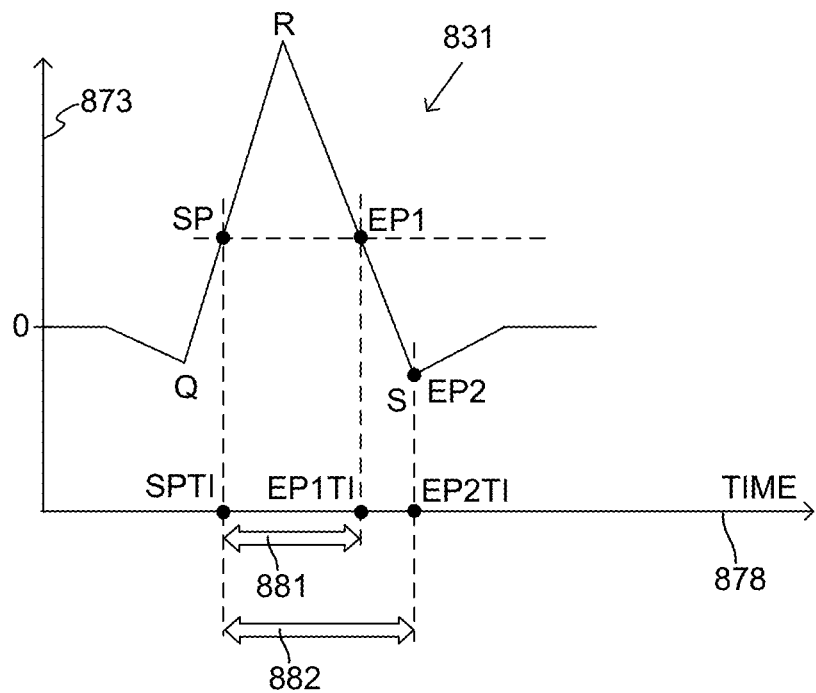
FIG. 8  *QRS WIDTH – SAMPLE DURATIONS*

*QRS WIDTH - SAMPLE STARTING POINTS FOR DURATION*

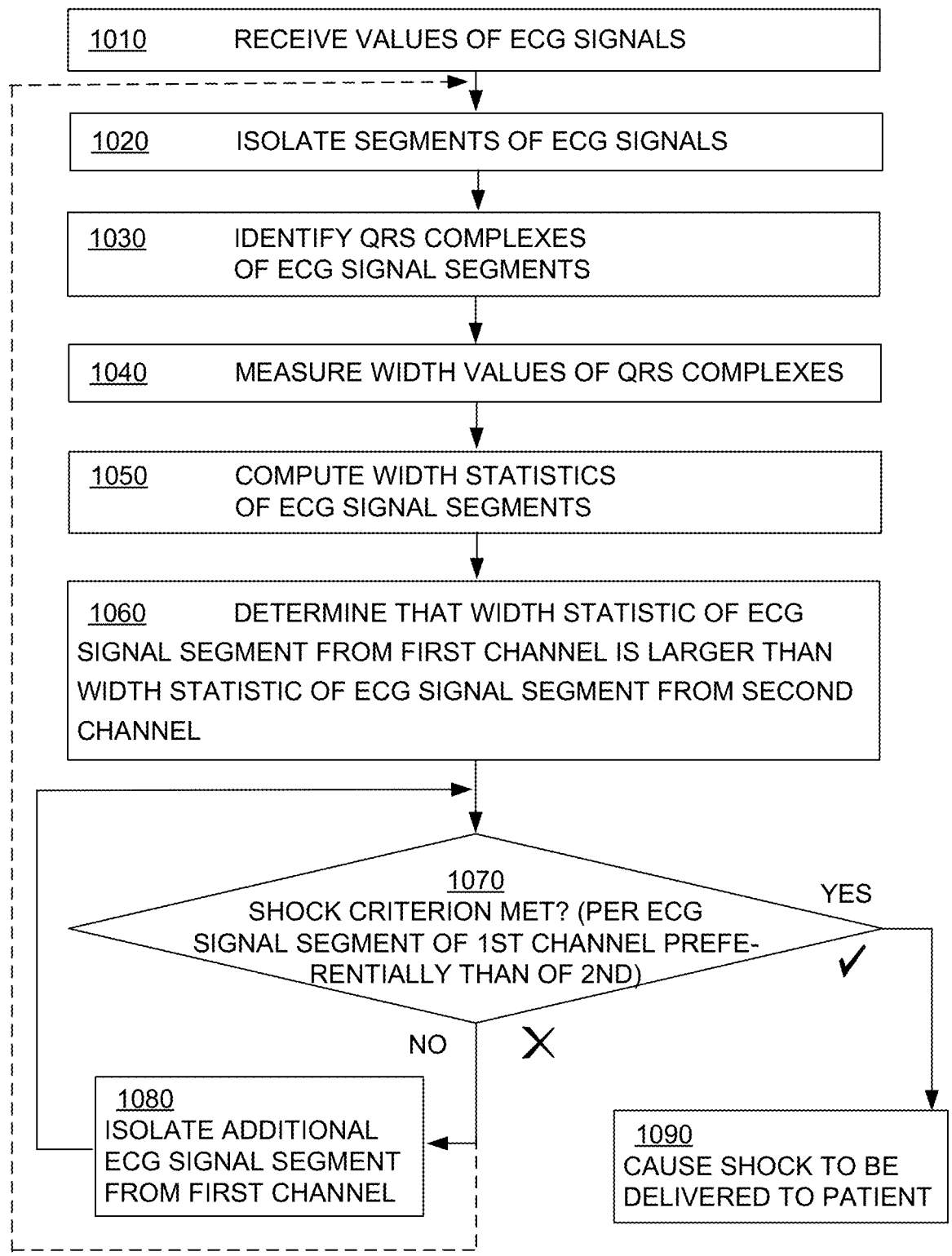
FIG. 10        *METHODS*

$$totalError(n) = \sum_{m=0}^{length(f)} (f(m) - g(n+m))\wedge 2$$

FIG. 13      *METHODS*

$$agreement(x) = \left(\sum_{y=1}^{4} e^{-\frac{-|(HR(x)-HR(y))|}{constant*HR(x)}}\right) - 1$$

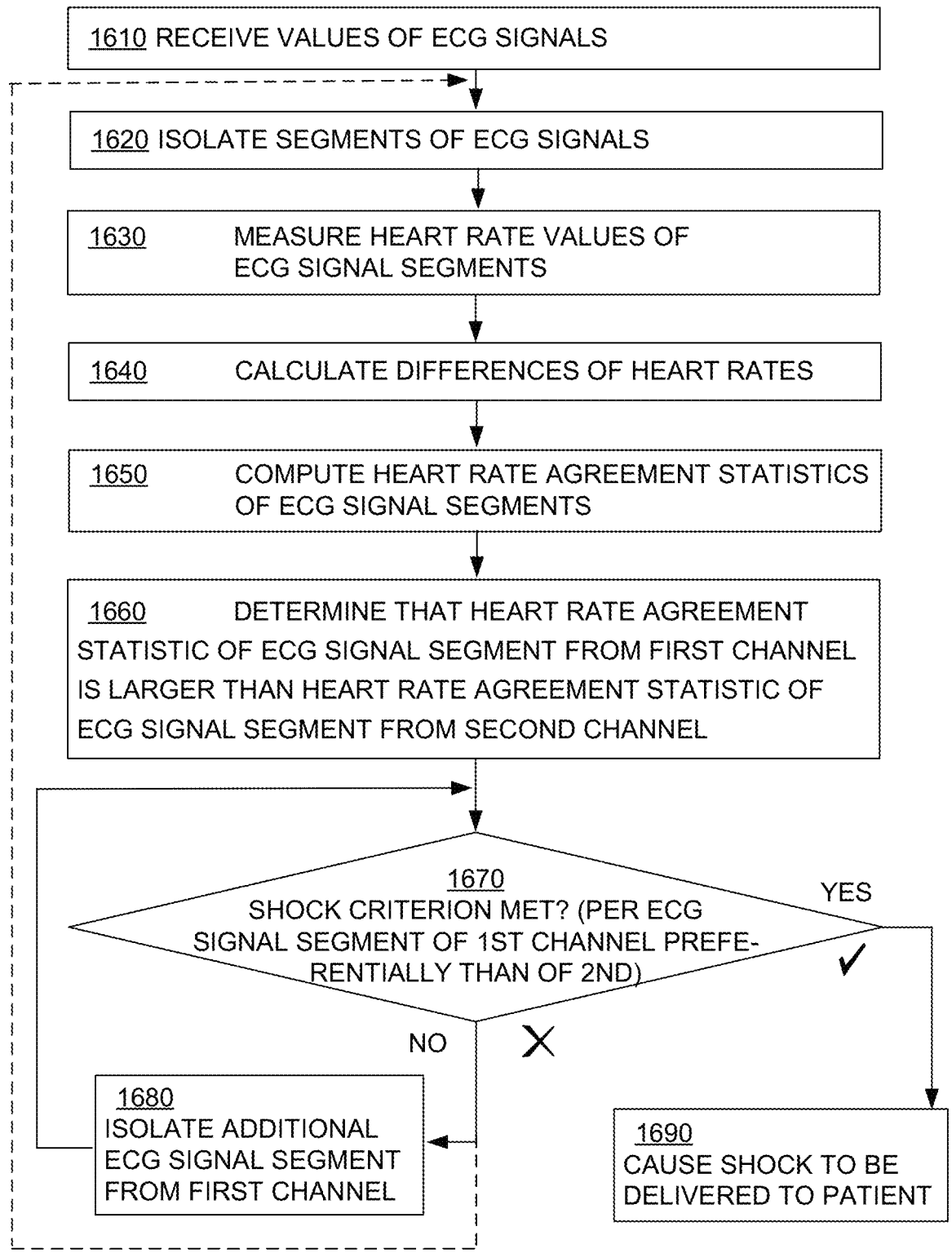
FIG. 16  *METHODS*

WEARABLE CARDIOVERTER DEFIBRILLATOR (WCD) SYSTEM CHOOSING TO CONSIDER ECG SIGNALS FROM DIFFERENT CHANNELS PER QRS COMPLEX WIDTHS OF THE ECG SIGNALS

CROSS REFERENCE TO RELATED PATENT APPLICATIONS

The present application is a continuation of U.S. application Ser. No. 16/366,313 filed Mar. 27, 2019 which is a divisional of U.S. application Ser. No. 16/268,870 filed Feb. 6, 2019 which in turn claims the benefit of U.S. application Ser. No. 62/630,398 filed on Feb. 14, 2018. Said application Ser. No. 16/366,313 claims the benefit of U.S. application Ser. No. 62/660,822 filed Apr. 20, 2018. Said application Ser. No. 16/268,870, said application Ser. No. 16/366,313, said application Ser. No. 62/660,822, and said application Ser. No. 62/630,398 are hereby incorporated herein by reference in their entireties.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present description gives instances of wearable cardioverter defibrillator (WCD) system, devices, systems, storage media that may store programs, and methods, the use of which may help overcome problems and limitations of the prior art.

In embodiments, a wearable cardioverter defibrillator (WCD) system includes a support structure for wearing by an ambulatory patient. When worn, the support structure maintains electrodes on the patient's body. Different pairs of these electrodes define different channels, and different patient ECG signals can be sensed from the channels. The ECG signals can be analyzed to determine which one is the best to use, for the WCD system to make a shock/no shock decision. The analysis can be according to widths of the QRS complexes, consistency of the QRS complexes, or heart rate agreement statistics.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 7 is a waveform amplitude diagram of that repeats a QRS complex identified in FIG. 6A, and indicates how a width of the a QRS complex can be measured according to embodiments.

FIG. 8 is a waveform amplitude diagram of a sample QRS complex, in larger magnification than the sample QRS complex of FIG. 7, where a sample starting point and two sample alternate ending points are identified on the waveform to indicate different possible ways to measure the width of the QRS complex, according to embodiments.

FIG. 10 is a flowchart for illustrating sample methods according to embodiments.

FIG. 16 is a flowchart for illustrating sample methods according to embodiments.

DETAILED DESCRIPTION

As has been mentioned, the present description is about wearable cardioverter defibrillator (WCD) system, devices, systems, storage media that may store programs, and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
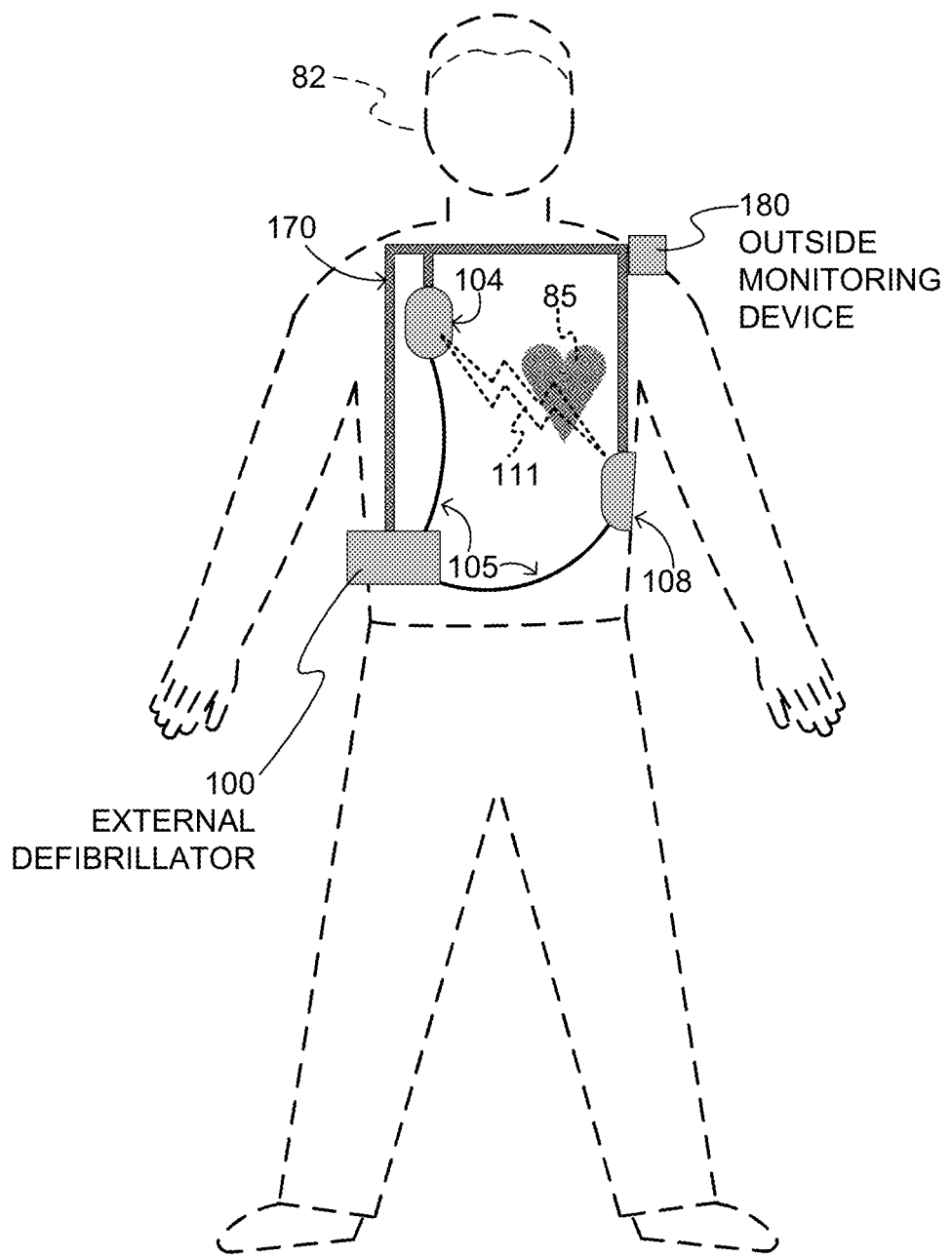
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the U52017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
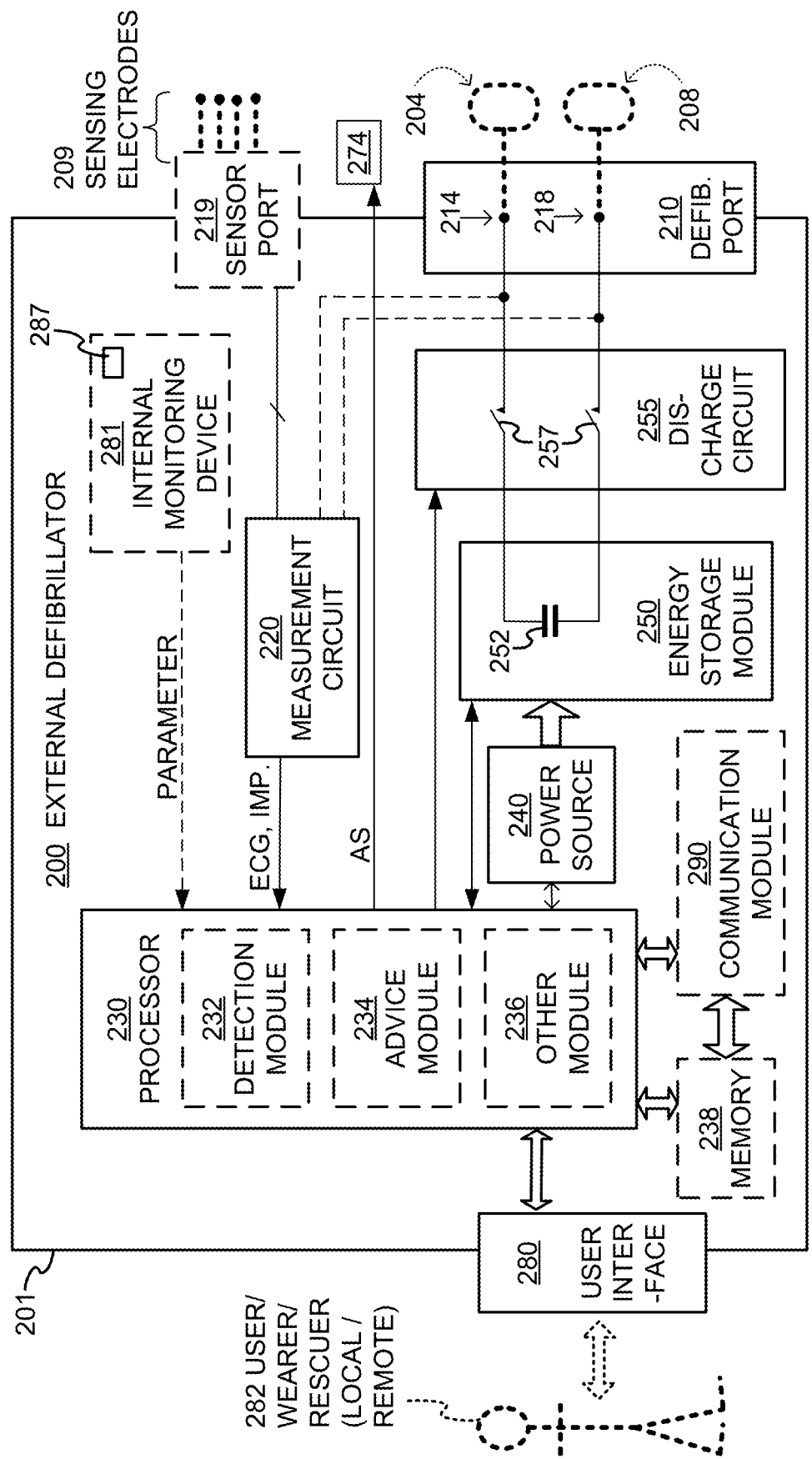
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
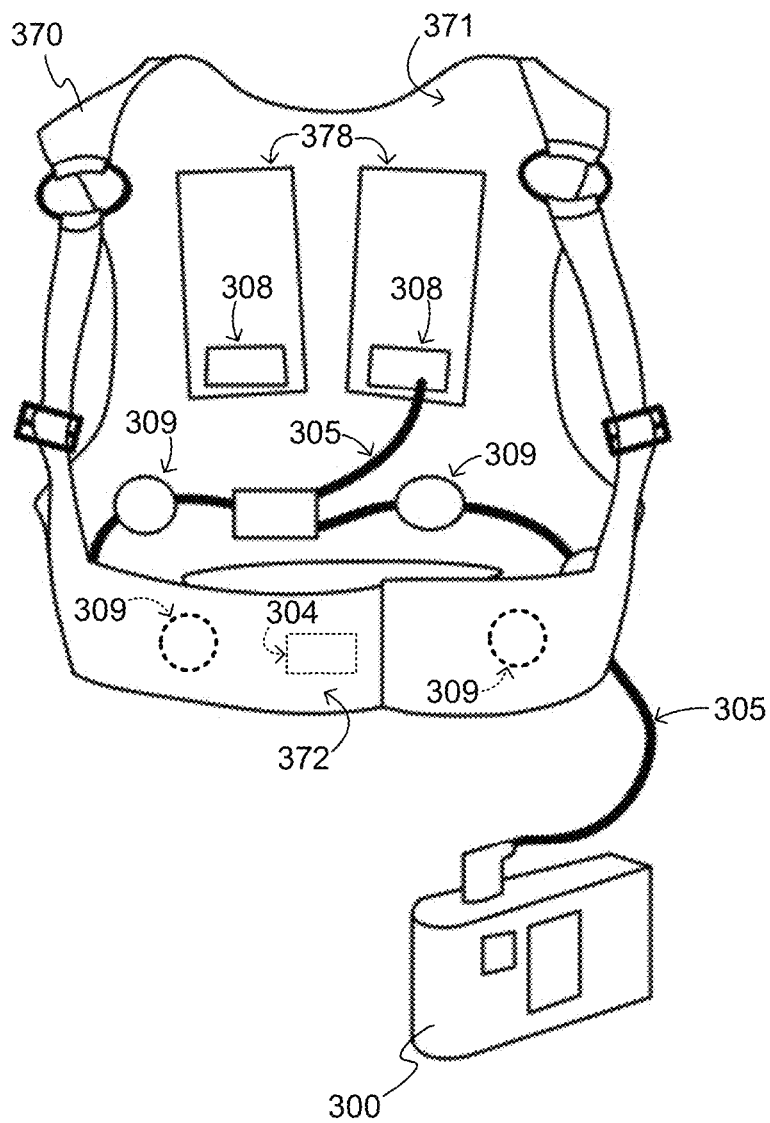
FIG. 3 is a diagram of sample embodiments of components of a WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
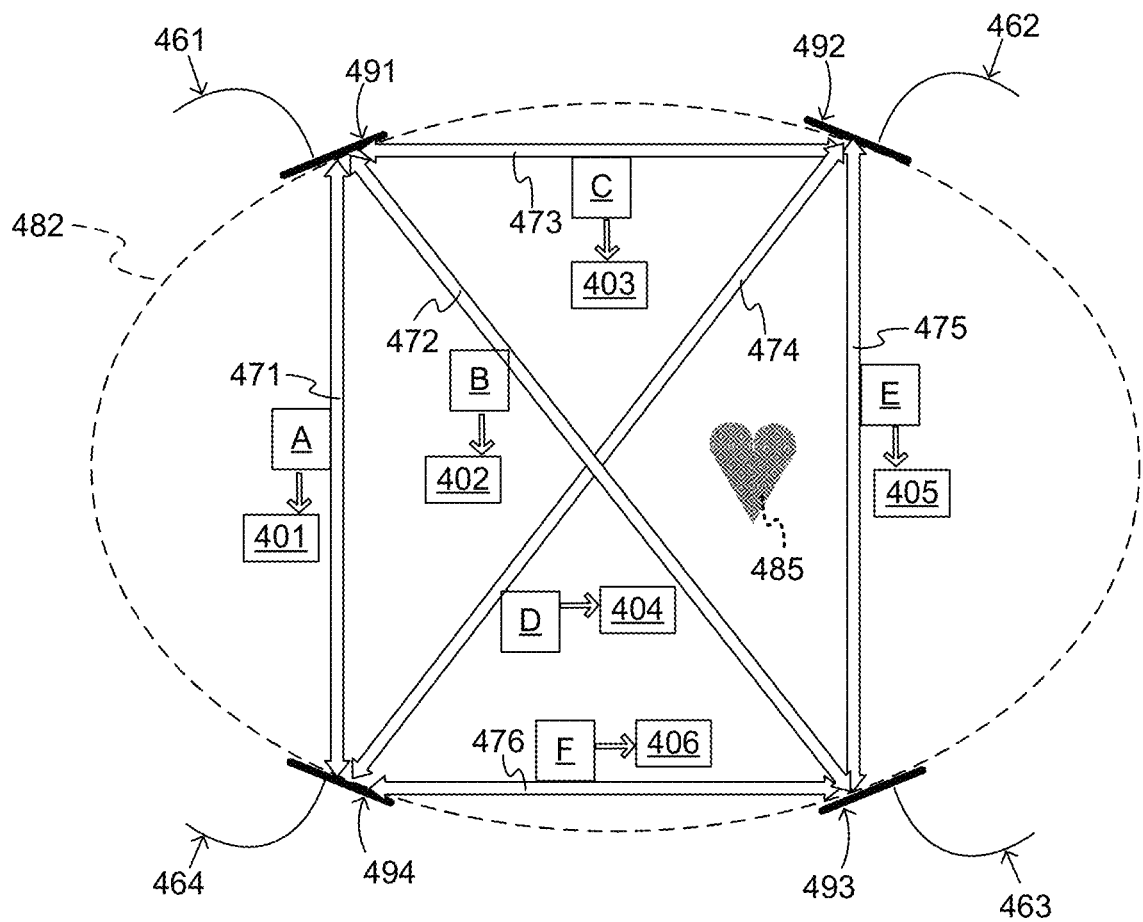
FIG. 4 is a conceptual diagram for illustrating an example how multiple electrodes may be used for sensing ECG signals along different vectors in a WCD system according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination. Examples are now described.

Figure 5:
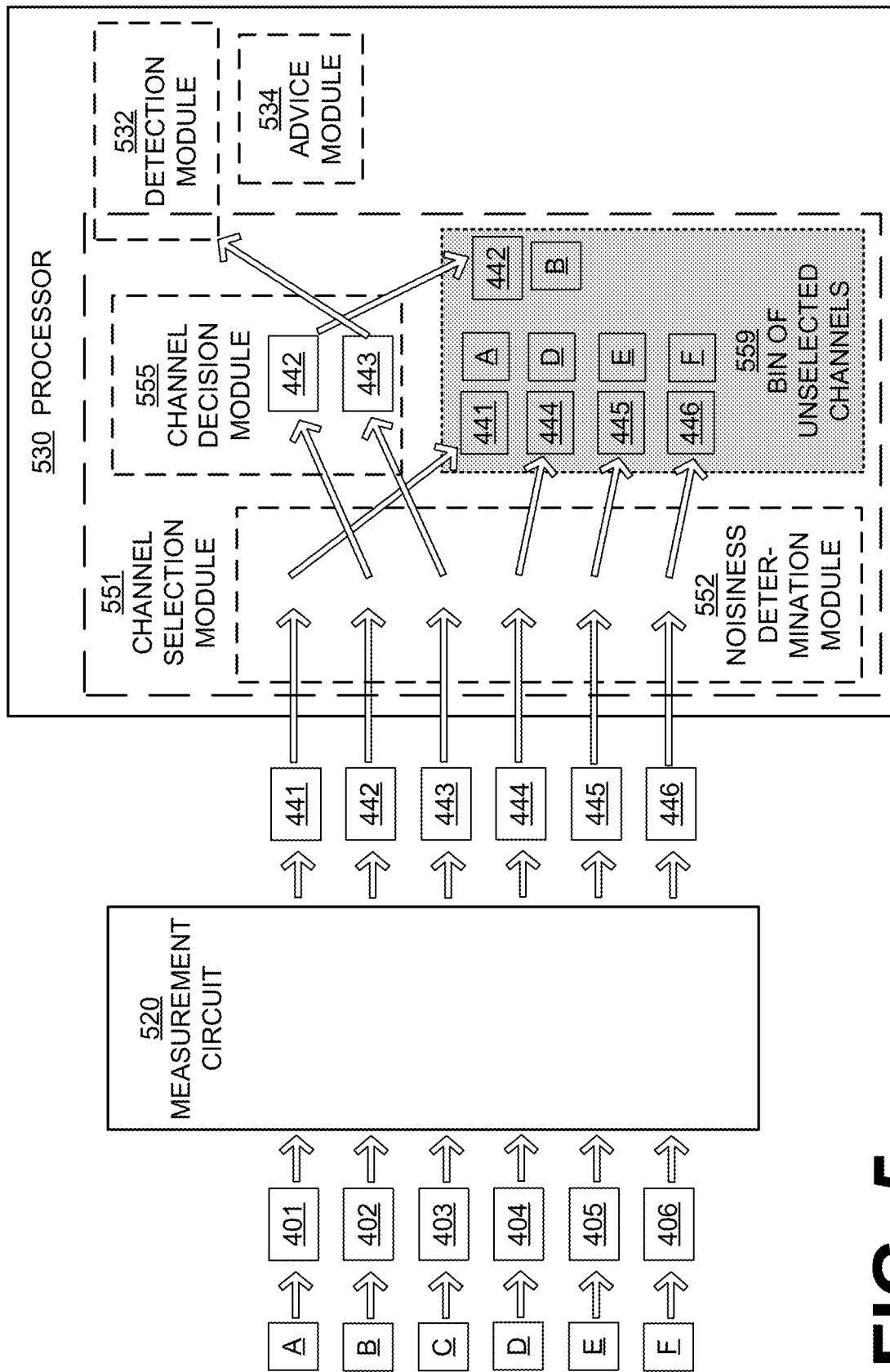
FIG. 5 is a diagram showing sample components of a WCD system, and sample embodiments of how channels are considered and selected according to their respective ECG signals.

FIG. 5 shows sample components of a WCD system, which include a measurement circuit 520 and a processor 530 that has a detection module 532 and an advice module 534. These can be similar to what was described earlier for measurement circuit 220, processor 230, detection module 232, and advice module 234 of FIG. 2.

In more detail, according to embodiments processor 530 also has a channel selection module 551, which selects one or more of the channels preferentially over the others for the detection at module 532 and advice at module 534. Detection module 532 is shown partially overlapping channel selection module 551 to denote that, in some embodiments, detection at module 532 happens for more than one signal, and the selection of module 551 happens after seeing the results of detection. In other embodiments, however, data from the ECG signals are not considered at this late stage, but are disqualified and disregarded at an earlier stage.

In addition, channels A, B, C, D, E, F can be similar to those described earlier in FIG. 4. ECG signals 401, 402, 403, 404, 405, 406 are sensed from respective channels A, B, C, D, E, F by measurement circuit 520. In turn, measurement circuit 520 renders values 441, 442, 443, 444, 445, 446, which are in turn received by processor 530. In particular, values 441, 442, 443, 444, 445, 446 are received by channel selection module 551. As will be seen later in this document, values 441, 442, 443, 444, 445, 446 can be waveform amplitude values of ECG signals 401, 402, 403, 404, 405, 406, with time coordinates being the ordinal number of the sample. The distance between successive time coordinates will of course depend on the sampling rate.

Module 551 includes a channel decision module 555, an optional noisiness determination module 552, and an optional conceptual bin of unselected channels 559. Bin 559 is for designating which channels are finally not used, along with the values of their signals.

Of these values 441, 442, 443, 444, 445, 446, one of them is selected to be considered. In some embodiments, module 552 is not provided and all channels are received by module 555. Since, however, in this example noisiness determination module 552 is actually provided, these values 441, 442, 443, 444, 445, 446 are first vetted for noise. This module 552 preliminarily analyzes the ECG signal values 441, 442, 443, 444, 445, 446, and determines that four of them have noise above a threshold. As such, module 552 routes the noisy four to bin 559, along with the channels A, D, E, F that their ECG signals came from. Module 552 also promotes the remaining two, namely signals 402, 403 from channels B, C and having values 442, 443, to channel decision module 555.

In this example, channel decision module 555 selects ECG values 443 for consideration, and accordingly inputs them in detection module 532. Remaining ECG values 442 are not selected for consideration, which is indicated graphically by routing them to bin 559, along with channel B that their ECG signal came from. The embodiments of FIG. 5 may be implemented in a number of ways.

Figure 6A:
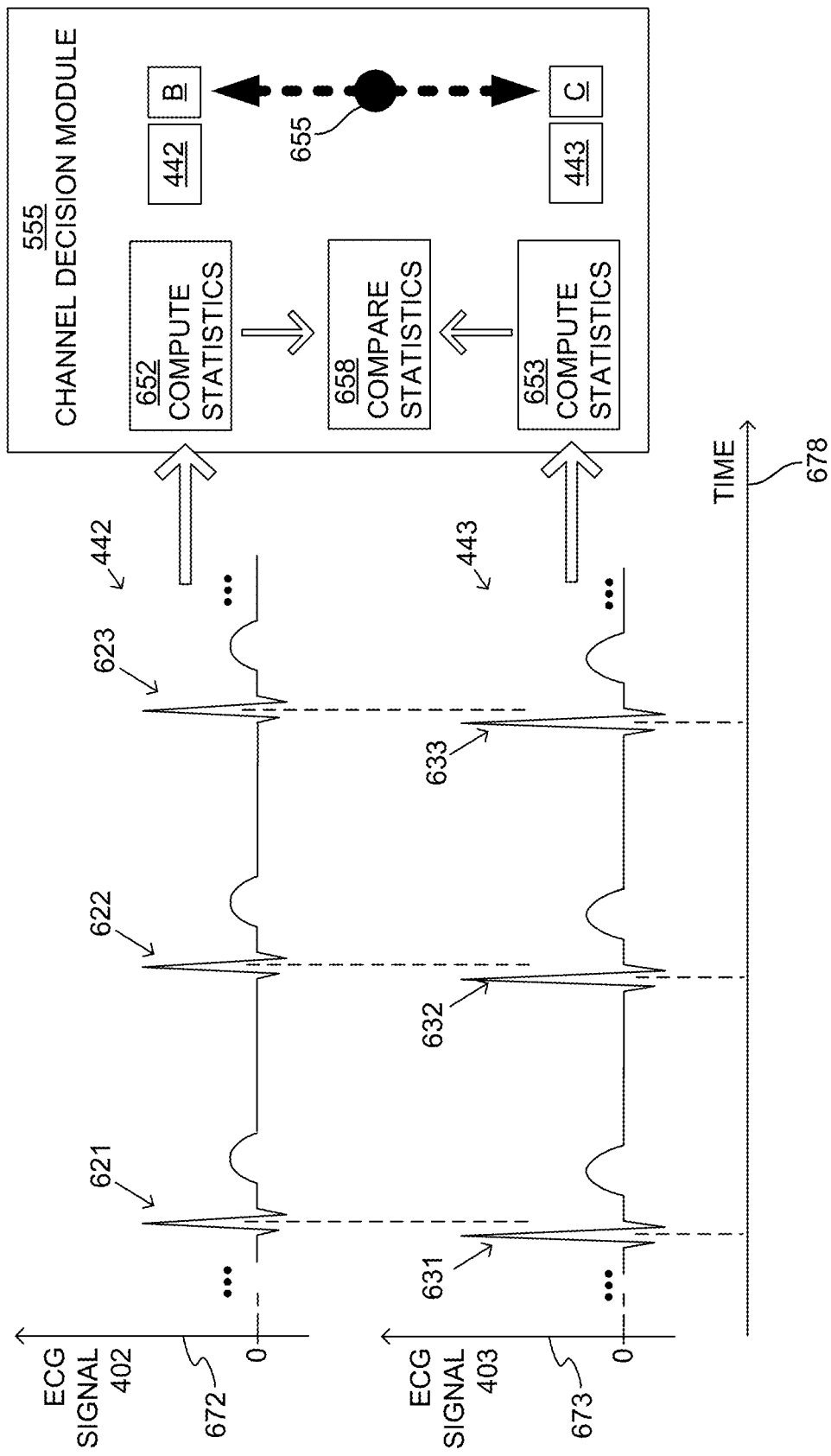
FIGS. 6A and 6B used for illustrating sample details of operations of a channel decision module of FIG. 5, according to embodiments.
Figure 6B:
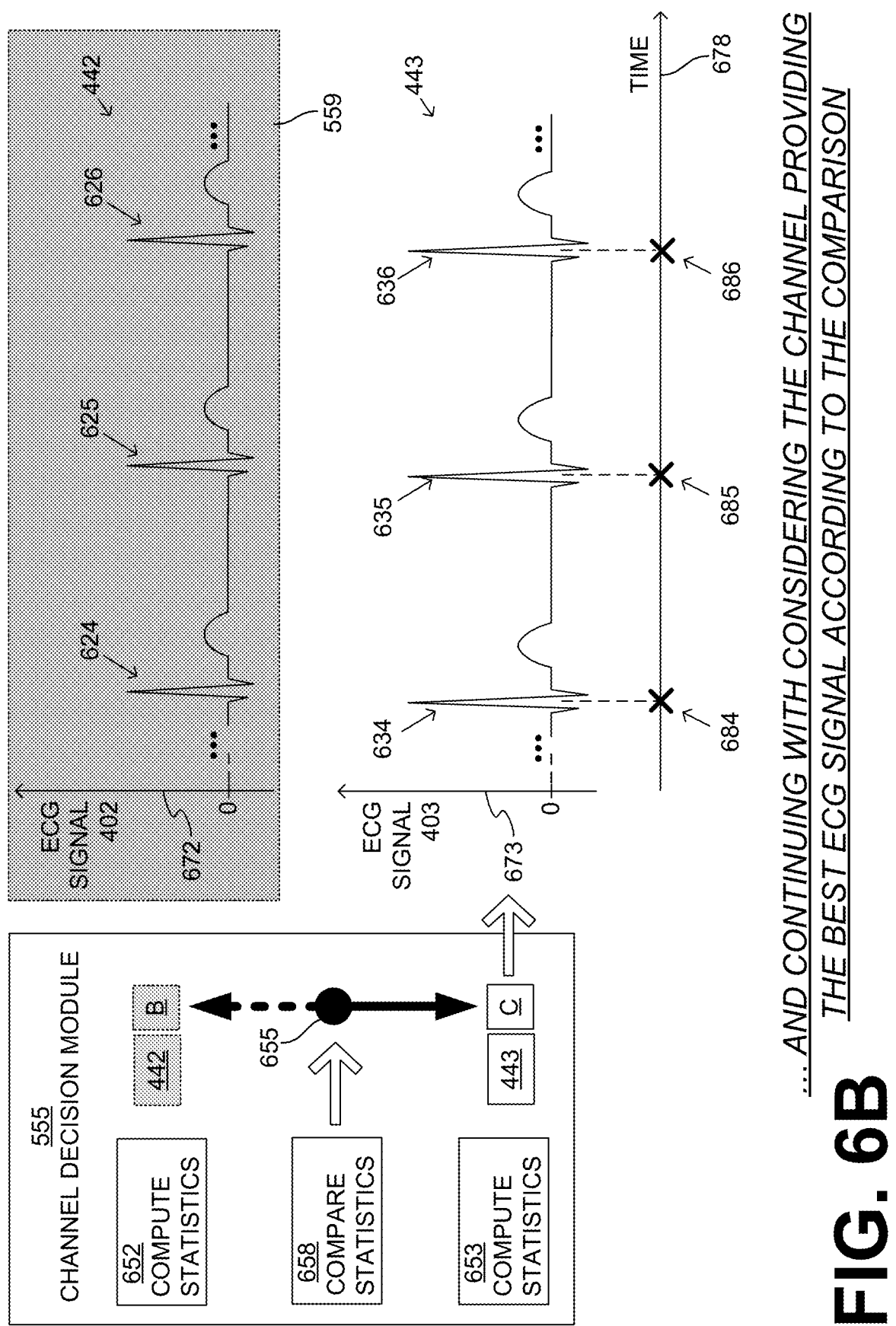

FIGS. 6A, 6B are used for illustrating sample operations of channel decision module 555. As seen in FIG. 6A, channel decision module 555 is receiving values 442, 443 of ECG signals 402, 403 respectively. Values 442, 443 are shown plotted against a shared horizontal time axis 678. Values 442 are shown plotted against a vertical amplitude axis 672, while values 443 are shown plotted against a vertical amplitude axis 673.

In embodiments, segments of the received ECG signals are isolated, for example by processor 530. Such isolating may be performed according to time intervals, for example segments having a 5 sec duration may be isolated. In the example of FIG. 6A, it will be understood that ECG signal segments shorter than 5 sec are shown due to space constraints, but without loss of generality.

In embodiments, QRS complexes of the ECG signal segments may be identified, for example by processor 530. Identification may be based on the received values 442, 443, for example for looking at R peaks in the signals, for values to be rising and falling steeply in the vicinity of such R peaks, etc. From values 442, QRS complexes 621, 622, 623 can be identified. From values 443, QRS complexes 631, 632, 633 can be identified. In this example, the waveforms of values 442, 443 are idealized in some ways. For example, they are shown with absolutely no noise, although this is not always the case, even if these waveforms have been promoted by module 552.

Within channel decision module 555, a decider arrow 655 has the option of pointing to either one of candidate channels B and C and, correspondingly, the values 442, 443 of their ECG signals. In FIG. 6A, decider arrow 655 points to neither one of them yet.

According to an operation 652, statistics of values 442 are computed, and according to an operation 653, statistics of values 443 are computed. Many different types of such statistics may be computed according to embodiments, and examples are given later in this document. The statistics computed at operations 652, 653 can then be compared per operation 658.

As seen in FIG. 6B, within channel decision module 555, responsive to the comparison at operation 658, decider arrow 655 now points to channel C. As such, the remainder of values 442 are relegated to bin 559, while the remainder of values 443 are promoted to the next stage, per FIG. 5, for determining whether or not to shock. These embodiments can be implemented in a number of ways.

The example of FIGS. 6A and 6B suggests that a channel selection for consideration decision is made from the earlier ECG segments of FIG. 6A according to the comparison of operation 658, and then subsequent segments of the selected channel are used for determining whether or not to shock. This is apparent because, in FIG. 6B, values 442 are shown with subsequently identified QRS complexes 624, 625, 626. And, values 443 are shown with subsequently identified QRS complexes 634, 635, 636.

In other embodiments, a channel selection for consideration decision is made from the earlier ECG segments of FIG. 6A, and then those same segments are used for determining whether or not to shock. In such an example, for instance, the earlier QRS complexes 631, 632, 633 of FIG. 6A would be used for determining whether or not to shock.

In either case, determining whether or not to shock can be implemented by determining whether or not a shock criterion is met. This shock/no shock determination can be made from a first ECG signal segment received from the thus selected for consideration channel C, preferentially than from a second ECG signal segment received from the other channel B that was not selected for consideration. By preferentially, it is meant that attributes of the first ECG signal are weighted more heavily in making the shock/no shock determination, than such attributes of the second ECG signal segment. This preference can be made responsive to the previous determination of which ECG signal's statistic was larger or smaller, per operation 658.

As such, in some embodiments attributes of both the first ECG signal and the second ECG signal are considered, albeit by different preferences, as per the above. In other embodiments, this second ECG signal segment that is not preferred is disregarded completely. As such, the shock/no shock determination can be made from the first ECG signal segment, but not from the second ECG signal segment.

In the example of FIG. 6B, given the selection of values 433, time intercepts 684, 685, 686 can be identified on time axis 678. As such, a heart rate value can be measured for ECG signal 403, and in particular for values 443, from time intercepts 684, 685, 686. And, in embodiments were ECG signal values are considered also for later stages, a heart rate value can also be measured for ECG signal 402, from values 442, before deciding which signal to use for determining whether or not to shock.

Returning to operations 652 and 653, many different types of such statistics may be computed for the ECG signals according to embodiments, for comparison at operation 658. Examples are now described of such statistics, each of which can be used by itself or in combination with one or more of these or other statistics.

In some embodiments, the statistics computed at operations 652 and 653 are width statistics of the respective segments of ECG signals 402, 403. These statistics can be computed from widths of the QRS complexes of the ECG signal segments. As such, width values of the QRS complexes may first be measured. A general example is now described.

FIG. 7 is a waveform amplitude diagram 703. Diagram 703 repeats QRS complex 631 that was identified in FIG. 6A. The baseline value is indicated as zero amplitude.

Generally, the width of QRS complex 631 will be a duration 780 that is measured on horizontal time axis 678. It will be observed that duration 780 is drawn somewhat coarsely, and refinements are presented later in this document.

From FIG. 7 it occurs that the units of width of a QRS complex are units of time. Moreover, if a constant rate of sampling of the ECG signal has been maintained, then the width can be computed more simply as a difference between ordinal numbers of a starting sample and an ending sample.

Then, from the measured widths, width statistics of segments of ECG signals 402, 403 may be computed. The width statistic of a particular one of the ECG signal segments can be computed according to the measured width values of certain ones of the QRS complexes of the particular ECG signal segment. In other words, the widths of not all QRS complexes might be considered, or the widths of all QRS complexes might be considered. As such, the width statistic of a segment of ECG signal 402 that has values 442 can be computed according to the measured width values of QRS complexes 621, 622, 623, and so on. That width statistic can be computed from the average of the width values, their median, and so on.

In such embodiments, the comparison of operation 658 is for determining which of the ECG signals has the larger width statistic. In other words, the one ECG signal segment that is preferred, here ECG signal 403 over ECG signal 402, is the one with the larger QRS widths, as determined by the width statistic. So, here the determination can be that the width statistic of a first one of the ECG signal (403) segments that was sensed from a first one of the channels (C), is larger than the width statistic of a second one of the ECG signal (402) segments that was sensed from a second one of the channels (B). Responsive to that, the determination of whether or not the shock criterion is met is made from the segment of ECG signal 403 preferentially than from the segment of ECG signal 402.

In some embodiments, processor 230 is further configured to determine a final width value from the measured width values of the QRS complexes of the ECG signal segment received from the first, preferred channel. In such embodiments, the determination of whether or not a shock criterion is met can be made from the final width value. For example, if the final width value is larger than a threshold, then the shock criterion is met, else it is not met. In some of these embodiments, the final width value is the width statistic from the ECG signal segment received from the selected channel (C). In other embodiments, the final width value uses this width statistic, and further adjustments are made.

This final width value may be used as a criterion alone, or in conjunction with other criteria. For example, in some embodiments processor 230 is further configured to measure a heart rate value of the ECG signal segment received from the first, preferred channel. This measuring can be from the QRS complexes in the ECG signal segments, for instance as described with reference to time intercepts 684, 685, 686. Processor 230 may then further determine a final heart rate value from the measured heart rate values. The final heart rate value may be the same as the measure a heart rate value, or adjusted for some factors, and so on. In such embodiments, then, the determination of whether or not a shock criterion is met can be made also from the final heart rate value.

If it is determined that the shock criterion is met, then processor 230 can be further configured to cause, responsive thereto, at least some of the electrical charge stored in energy storage module 250 to be discharged via at least one of the electrodes through ambulatory patient 82, so as to deliver a shock 111 to ambulatory patient 82.

Refinements are now being described for how the QRS width may be measured. For such, a starting point and an ending point can be defined on an amplitude waveform of a particular QRS complex. The width value of the particular QRS complex can be determined as a time duration from a difference of time intercepts of the ending point and the starting point. The starting point and the ending point can be defined in different ways. Examples are now described.

FIG. 8 is a waveform amplitude diagram having an amplitude axis 873 and a time axis 878. A sample QRS complex 831 is shown, relative to a baseline that is indicated as zero on axis 873. QRS complex 831 is in larger magnification than QRS complex 631, for more clarity.

A sample starting point SP and two sample alternate ending points EP1, EP2 are identified on waveform of QRS pulse 831. Ending point EP1 has the same value on axis 873 as starting point SP, and defines a width 881 from time intercepts SPTI and EP1TI. For alternate ending point EP2, however, the amplitude waveform does not have the same value as the amplitude waveform has at starting point SP. Still, a different width 882 can be defined according to embodiments.

Figure 9:
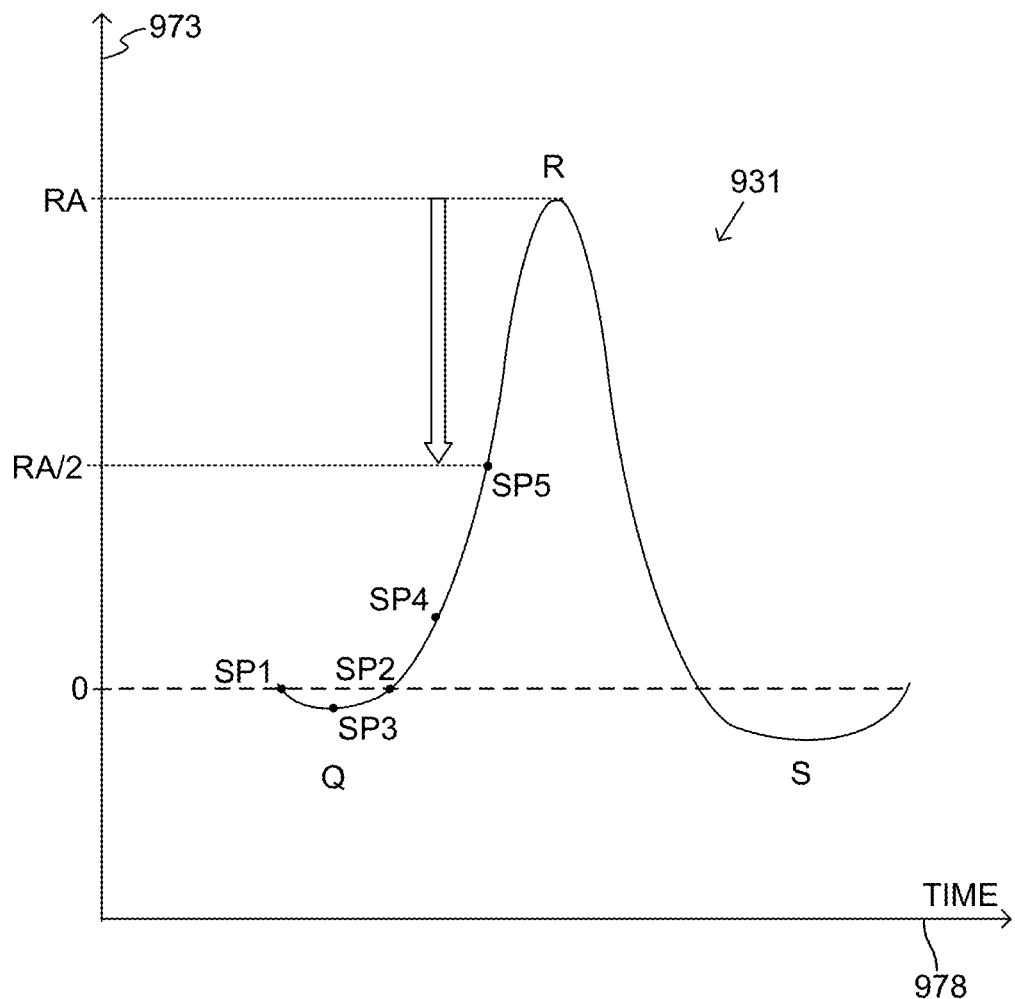
FIG. 9 is a waveform amplitude diagram of a sample QRS complex, in larger magnification than the sample QRS complex of FIG. 8, where multiple sample starting points are identified on the waveform to indicate different possible ways to measure the width of the QRS complex, according to embodiments.

FIG. 9 is a waveform amplitude diagram having an amplitude axis 973 and a time axis 978. A sample QRS complex 931 is shown. QRS complex 931 is in larger magnification than QRS complex 831, to demonstrate additional refinements according to embodiments.

In some embodiments, a baseline of the ECG signal segment that includes the particular QRS complex is determined. In this example, the baseline is indicated as zero on axis 973. In such embodiments, the starting point and/or the ending point can be defined from a time when a waveform of the particular QRS complex crosses the baseline. In the example of FIG. 9, such possible starting points are indicated as SP1, SP2. Ending points can be defined similarly.

In some embodiments, the starting point is defined from a time intercept of a negative Q peak of the particular QRS complex. In the example of FIG. 9, such a possible starting point is indicated as SP3. Additionally, the ending point can be defined from a time intercept of the negative S peak of the particular QRS complex.

In some embodiments, a slope of the particular QRS complex is computed. In such embodiments, the starting point and/or the ending point can be defined from a time when an absolute value of the slope exceeds a threshold. In the example of FIG. 9, such a possible starting point is indicated as SP4. An ending point can be defined similarly.

In some embodiments, an amplitude of an R peak of the particular QRS complex can be determined. In such embodiments, the starting point and/or the ending point can be defined from a time when a waveform of the particular QRS complex equals a fraction of the amplitude. In the example of FIG. 9, the R peak of QRS complex 931 has an amplitude RA, and a possible starting point that has amplitude RA/2 is indicated as SP5. The fraction is half. An ending point can be defined similarly.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

FIG. 10 shows a flowchart 1000 for describing methods according to embodiments. As will be recognized, many of the operations of flowchart 1000 can be performed as described above.

According to an operation 1010, the values of the ECG signals may be received. According to another, optional operation 1020, segments of the received ECG signals may be isolated.

According to another operation 1030, QRS complexes of the ECG signal segments may be identified. Identification may be performed based on the received values.

According to another operation 1040, width values of the QRS complexes may be measured.

According to another operation 1050, width statistics of the ECG signal segments may be computed. The width statistic of a particular one of the ECG signal segments may be computed according to the width values of certain ones of the QRS complexes measured at operation 1040 for the particular ECG signal segment.

According to another operation 1060, it may be determined that the width statistic of a first one of the ECG signal segments that was sensed from a first one of the channels, is larger than the width statistic of a second one of the ECG signal segments that was sensed from a second one of the channels. This determination may be responsive to a comparison, such as the comparison of operation 658.

According to another, optional operation 1070, it can be determined whether or not a shock criterion is met. Responsive to the determination of operation 1060, the determination of operation 1070 can be made from an ECG signal segment received from the first channel preferentially than from an ECG signal segment received from the second channel.

If, at operation 1070 the answer is YES, then according to another operation 1090, at least some of the stored electrical charge can be caused to be discharged via at least one of the electrodes through the ambulatory patient so as to deliver a shock to the ambulatory patient.

If, at operation 1070 the answer is NO, then execution may return to operation 1020. Or, instead, according to another, optional operation 1080, an additional ECG segment from the selected first channel may be isolated, and execution then can return to operation 1070.

In some embodiments, the statistics computed at operations 652 and 653 are self-similarity statistics of the respective segments of ECG signals 402, 403. These statistics can be computed from differences in amplitude waveform values from reference QRS complexes of the ECG signal segments. As such, reference QRS complexes can be first identified or computed, and then stored in memory 238. Then the differences in amplitude waveform values can be computed, and so on. In some embodiments, a WCD system may choose to consider ECG signals from different channels per QRS complex consistencies of the ECG signals. The consistency may be determined from the self-similarity statistics. Such notions may be found to be related to the notion of QRS organization.

The above-mentioned reference QRS complexes can be identified or computed in a number of ways. For example, the reference QRS complex for a certain one of the ECG signal segments can be one of the QRS complexes of the certain ECG signal segment.

In some embodiments, processor 230 is further configured to compute the reference QRS complex for a certain one of the ECG signal segments from amplitude waveform values of some or all of the QRS complexes of the certain ECG signal segment. For example, the reference QRS complex can be computed as an average of amplitude waveform values of all the QRS complexes of the certain ECG signal segment. An example is now described.

Figure 11A:
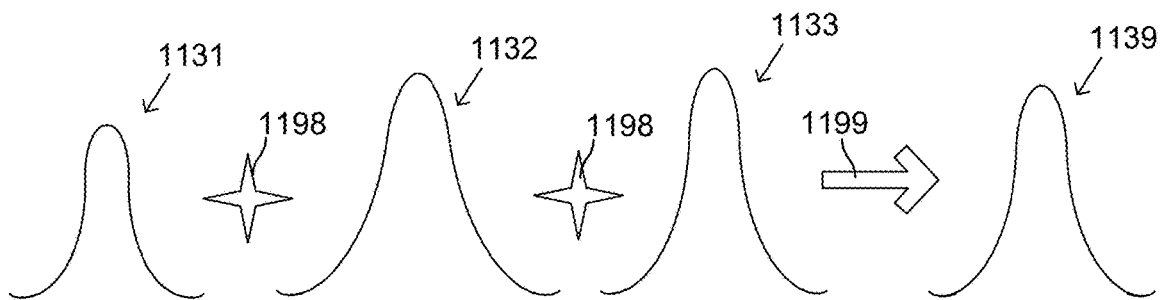
FIGS. 11A-11C depict conceptually a sample way of how self-similarity statistics of considered ECG signal segments may be computed based on their respective QRS complexes according to embodiments.
Figure 11B:
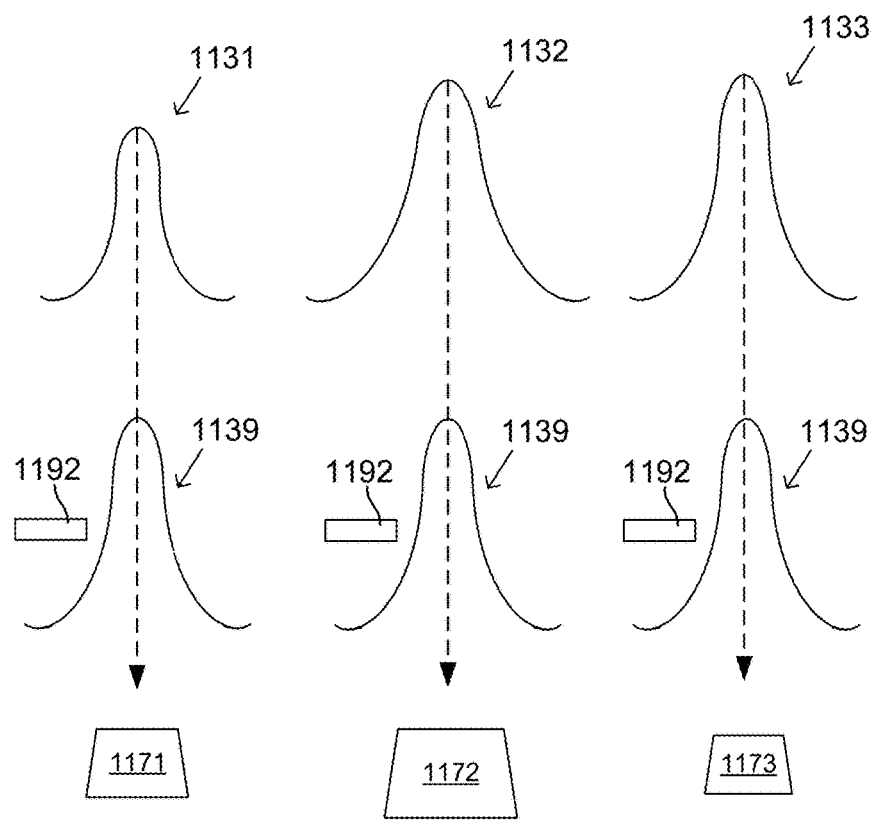
Figures 11C, 12:
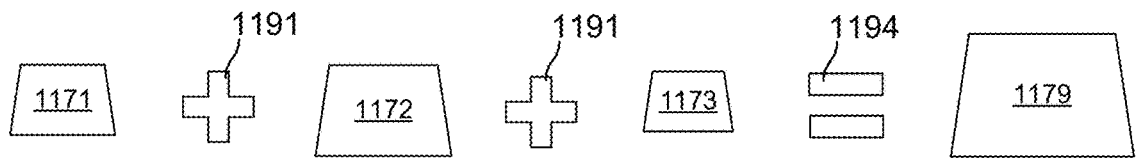
FIG. 12 shows a sample mathematical equation for implementing an operation of the calculation of FIG. 11B according to an embodiment.

FIGS. 11A-11C depict conceptually a sample way of how self-similarity statistics of considered ECG signal segments may be computed. FIG. 11A shows three sample QRS complexes 1131, 1132, 1133, which are being used to compute, according to an arrow 1199, a reference QRS complex 1139. QRS complexes 1131, 1132, 1133 are shown as being combined by stars 1196, as if the stars were plus signs. In embodiments where reference QRS complex 1139 is computed from an average, then stars 1196 could indeed be plus signs, and a division by 3 would have to be further indicated. QRS complexes 1131, 1132, 1133 are from a single ECG signal segment, and reference QRS complex 1139 is the reference QRS complex for that single ECG signal segment. Such reference QRS complexes may be computed for respective ECG signal segments.

FIG. 11B shows differences being calculated in amplitude waveform values of QRS complexes 1131, 1132, 1133 from amplitude waveform values of reference QRS complex 1139. The subtractions are indicated by minus signs 1192. The computed individual differences are indicated by respective shapes 1171, 1172, 1173.

FIG. 11C shows a self-similarity statistic 1179 of an ECG signal segment being computed. In general, self-similarity statistic 1179 is computed according to calculated differences 1171, 1172, 1173. In this example, self-similarity statistic 1179 is computed by adding calculated differences 1171, 1172, 1173 using plus signs 1191 and an equals sign 1194. Again, self-similarity statistics may be computed for the respective ECG signal segments.

FIG. 12 shows a mathematical equation for the calculation of the differences of FIG. 11B. Differences 1271, 1272, 1273 could be differences 1171, 1172, 1173. Each can be computed as a total error, over the duration of the waveform, of a squared difference. That difference is of the amplitude of the QRS complexes f( )1231, 1232, 1233 from the reference g( )1239. Of course, in this case, QRS complexes 1231, 1232, 1233 could be QRS complexes 1131, 1132, 1133, etc.

In such embodiments, the comparison of operation 658 is for determining which of the ECG signals has the smallest self-similarity statistic, which corresponds to the largest consistency. In other words, the one ECG signal segment that is preferred, here ECG signal 403 over ECG signal 402, is the one whose QRS segments differ least from their reference. So, here the determination can be that the self-similarity statistic of a first one of the ECG signal (403) segments that was sensed from a first one of the channels (C), is less than the self-similarity statistic of a second one of the ECG signal (402) segments that was sensed from a second one of the channels (B). Responsive to that, the determination of whether or not the shock criterion is met is made from the segment of ECG signal 403 preferentially than from the segment of ECG signal 402.

Figure 13:
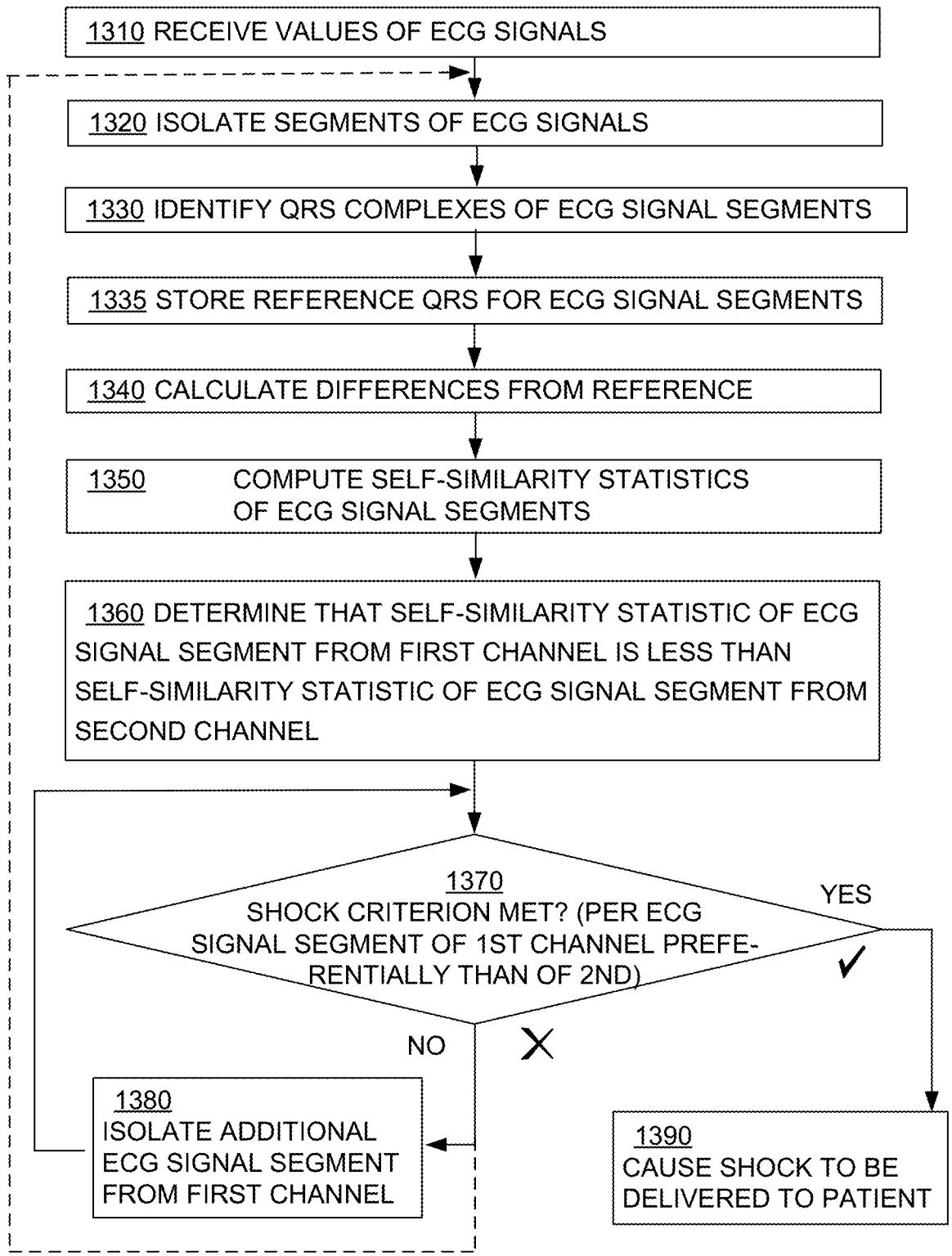
FIG. 13 is a flowchart for illustrating sample methods according to embodiments.

FIG. 13 shows a flowchart 1300 for describing methods according to embodiments. Again, many of the operations of flowchart 1300 can be performed as described above. In addition, operations 1310, 1320, 1330 can be performed as described for operations 1110, 1120, 1130 respectively.

According to another, optional operation 1335, reference QRS complexes are stored for the ECG signal segments. This may be performed after reference QRS complexes have been identified, or computed, for instance as described for reference QRS complex 1139.

According to another operation 1340, differences in amplitude waveform values of the QRS complexes from their corresponding reference QRS complex may be calculated for the ECG signal segments.

According to another operation 1350, self-similarity statistics of the ECG signal segments may be computed. The self-similarity statistic of a particular one of the ECG signal segments may be computed according to the differences in amplitude waveform values calculated at operation 1340 for the particular ECG signal segment.

According to another operation 1360, it may be determined that the self-similarity statistic of a first one of the ECG signal segments that was sensed from a first one of the channels, is less than the self-similarity statistic of a second one of the ECG signal segments that was sensed from a second one of the channels. This determination may be responsive to a comparison, such as the comparison of operation 658.

In addition, operations 1370, 1380, 1390 can be performed as described for operations 1170, 1180, 1190, respectively. In some embodiments, the statistics computed at operations 652 and 653 are heart rate agreement statistics of the respective segments of ECG signals 402, 403. These statistics can be computed from differences of the heart rate values of the ECG signal segments. As such, heart rate values of the ECG signal segments may first be measured. In some embodiments, a WCD system may choose to consider ECG signals from different channels per heart rate agreement statistics of the ECG signals. An example is now described.

In some embodiments, therefore, heart rate values of the ECG signal segments are measured. In some embodiments, processor 230 is further configured to identify QRS complexes 634, 635, 636 of a particular one (443) of the ECG signal segments, and identify time intercepts 684, 685, 686 of R peaks of the QRS complexes. In such embodiments, time differences can be computed in successive pairs of time intercepts 684, 685, 686, and in which the heart rate values of the particular ECG signal segment is measured from the time differences. For example, the heart rate values can be found from the inverse of an average, a median, etc. of the time differences.

Figures 14, 15:
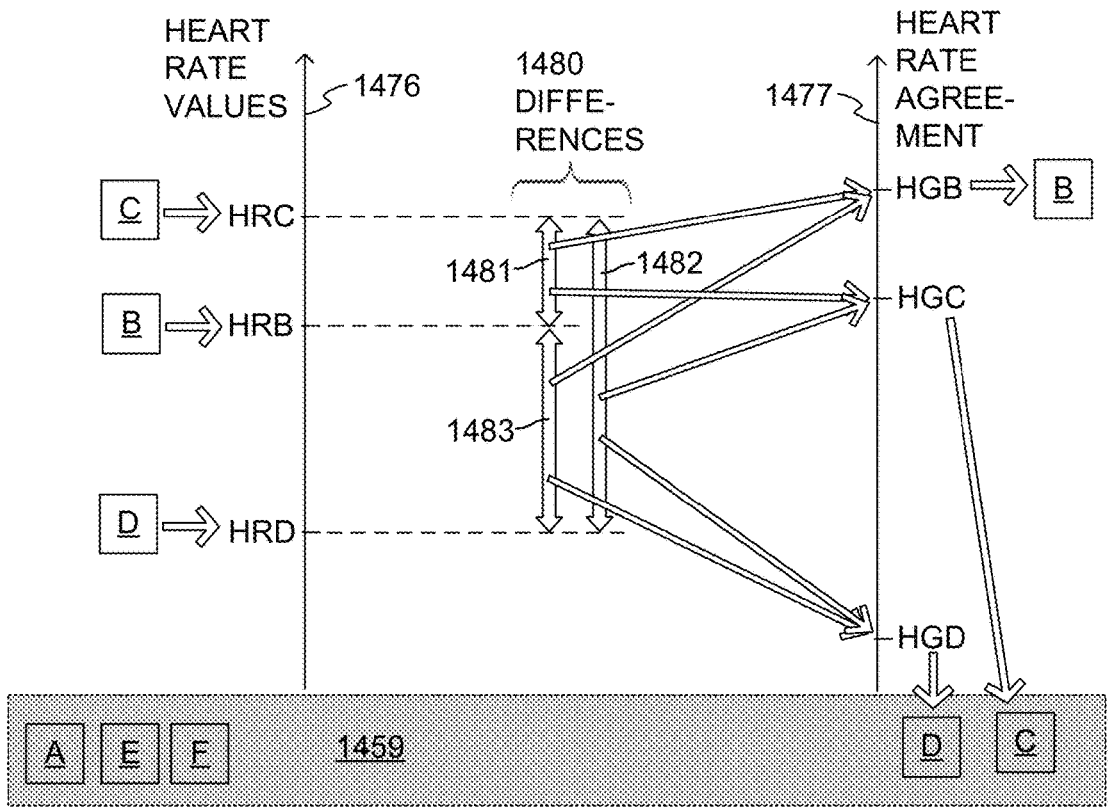
FIG. 14 depicts conceptually how heart rate agreement statistics of considered ECG signal segments may be computed based on their respective heart rates according to embodiments.
FIG. 15 shows a mathematical equation for a sample way of implementing a computation of FIG. 14.

FIG. 14 shows a sample scenario where the ECG signal segments from channels A, E, F have been found noisy, and have already been relegated to a bin 1459 that is similar to bin 559. In addition, for remaining considered channels B, C, D, heart rate values HRB, HRC, HRD have been measured. The heart rate values are plotted according to magnitude on a vertical axis 1476.

In embodiments, differences of heart rate values HRB, HRC, HRD among themselves are calculated. FIG. 14 also shows a group 1480 of such differences for remaining channels B, C, D. In particular, difference 1481 is the difference between HRC and HRB, difference 1482 is the difference between HRC and HRD, and difference 1483 is the difference between HRB and HRD.

In such embodiments, heart rate agreement statistics of the ECG signal segments can be computed. For example, the heart rate agreement statistic of a particular one of the ECG signal segments, say the one from channel B, can be computed from the calculated differences of the heart rate value of the particular ECG signal segment (HRB) from heart rate values of others of the ECG signal segments (HRC, HRD). As such, heart rate agreement statistics HGB, HGC, HGD can be computed, from components shown in FIG. 14. FIG. 14 also shows another vertical axis 1477, onto which heart rate agreement statistics HGB, HGC, HGD are plotted.

The heart rate agreement statistics can be computed in a number of ways. In some embodiments, the heart rate agreement statistic of a particular ECG signal segment, say HGB, is computed by adding the calculated differences of the heart rate value of the particular ECG signal segment from heart rate values of others of the ECG signal segments, e.g. from differences 1481 and 1483. Same with heart rate agreement statistics HGC and HGD.

In this example, processor 230 determines that HGB is larger than HGC and HGD. This, of course, is immediately apparent to a human simply looking at axis 1477. Responsive to that, channel B can be considered preferentially, as also per the above, while remaining channels D, C are also routed to bin 1459.

FIG. 15 shows a mathematical equation for a sample way of implementing the computation of heart rate agreement statistics, such as those of FIG. 14. The minus sign 1592 is for calculating differences 1480, and taking their absolute values. The summation is for the components that contribute to the final heart rate agreement statistic.

A number of variations are possible. For example, in some embodiments processor 230 can be further configured to determine a final heart rate value from measured heart rate values HRB, HRC, HRD. This final heart rate value can be an average, a median, etc. of the measured heart rate values. In such embodiments, the determination of whether or not the shock criterion is met can be made also from the final heart rate value.

FIG. 16 shows a flowchart 1600 for describing methods according to embodiments. Again, many of the operations of flowchart 1600 can be performed as described above. In addition, operations 1610, 1620 can be performed as described for operations 1110, 1120, respectively.

According to another operation 1630, heart rate values of the ECG signal segments may be measured. This can be performed as described above, for example for measuring HRB, HRC, HRD.

According to another operation 1640, differences of the heart rate values among themselves can be calculated. This can be performed as described above, for example for calculating differences 1481, 1482, 1483.

According to another operation 1650, heart rate agreement statistics of the ECG signal segments may be computed. This can be performed as described above, for example for computing heart rate agreement statistics HGB, HGC and HGD.

According to another operation 1660, it may be determined that the heart rate agreement statistic of a first one of the ECG signal segments that was sensed from a first one of the channels, is larger than the heart rate agreement statistic of a second one of the ECG signal segments that was sensed from a second one of the channels. This determination may be responsive to a comparison, such as the comparison of operation 658.

In addition, operations 1670, 1680, 1690 can be performed as described for operations 1170, 1180, 1190, respectively.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise.

Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system for an ambulatory patient, comprising:
an energy storage module configured to store an electrical charge;
electrodes;
a support structure configured to be worn by the ambulatory patient so as to maintain at least some of the electrodes on a body of the ambulatory patient, at least three distinct channels being defined by distinct respective pairs of at least some of the electrodes;
a measurement circuit configured to sense three electrocardiogram (ECG) signals of the patient from the three channels respectively, and to render values therefrom; and
a processor configured to:
receive the values of the ECG signals,
isolate segments of the received ECG signals,
measure heart rate values of the ECG signal segments,
calculate differences of the heart rate values among themselves,
compute heart rate agreement statistics of the ECG signal segments, the heart rate agreement statistic of a particular one of the ECG signal segments computed from the calculated differences of the heart rate value of the particular ECG signal segment from heart rate values of others of the ECG signal segments,
determine that the heart rate agreement statistic of a first one of the ECG signal segments that was sensed from a first one of the channels, is larger than the heart rate agreement statistic of a second one of the ECG signal segments that was sensed from a second one of the channels,
and responsive to the heart rate agreement determination, determine whether or not a shock criterion is met, the determination made from an ECG signal segment received from the first channel preferentially than from an ECG signal segment received from the second channel, and
cause, responsive to the shock criterion being met, at least some of the stored electrical charge to be discharged via at least one of the electrodes through the ambulatory patient so as to deliver a shock to the ambulatory patient.

2. The WCD system of claim 1, in which
the processor is further configured to:
identify QRS complexes of a particular one of the ECG signal segments,
identify time intercepts of R peaks of the QRS complexes,
compute time differences in successive pairs of the time intercepts, and
in which the heart rate value of the particular ECG signal segment is measured from the time differences.

3. The WCD system of claim 1, in which
the heart rate agreement statistic of the particular ECG signal segment is computed by adding the calculated differences of the heart rate value of the particular ECG signal segment from heart rate values of others of the ECG signal segments.

4. The WCD system of claim 1, in which the processor is further configured to:
identify QRS complexes in the ECG signals,
measure width values of the QRS complexes,
determine a final width value from the measured width values of the QRS complexes of the ECG signal segment received from the first channel, and
in which the determination of whether or not the shock criterion is met is made also from the final width value.

5. The WCD system of claim 1, in which the processor is further configured to:
determine a final heart rate value from the measured heart rate value of the ECG signal segment received from the first channel, and
in which the determination of whether or not the shock criterion is met is made also from the final heart rate value.

6. The WCD system of claim 1, in which
the determination of whether or not the shock criterion is met is made from an ECG signal segment received from the first channel but not from an ECG signal segment received from the second channel.

7. A non-transitory computer-readable storage medium storing one or more programs which, when executed by at least one processor of a wearable cardioverter defibrillator ("WCD") system, the WCD system further including an energy storage module configured to store an electrical charge, electrodes, a support structure configured to be worn by an ambulatory patient so as to maintain at least some of the electrodes on a body of the ambulatory patient, at least two distinct channels being defined by distinct respective pairs of at least some of the electrodes, and a measurement circuit configured to sense two electrocardiogram (ECG) signals of the patient from the two channels respectively and to render values therefrom, these one or more programs result in operations comprising:
receiving the values of the ECG signals,
isolating segments of the received ECG signals,
measuring heart rate values of the ECG signal segments,
calculating differences of the heart rate values among themselves,
computing heart rate agreement statistics of the ECG signal segments, the heart rate agreement statistic of a particular one of the ECG signal segments computed from the calculated differences of the heart rate value of the particular ECG signal segment from heart rate values of others of the ECG signal segments,
determining that the heart rate agreement statistic of a first one of the ECG signal segments that was sensed from a first one of the channels, is larger than the heart rate agreement statistic of a second one of the ECG signal segments that was sensed from a second one of the channels,
and responsive to the heart rate determining, determining whether or not a shock criterion is met, the determination made from an ECG signal segment received from the first channel preferentially than from an ECG signal segment received from the second channel, and
cause, responsive to the shock criterion being met, at least some of the stored electrical charge to be discharged via at least one of the electrodes through the ambulatory patient so as to deliver a shock to the ambulatory patient.

8. The medium of claim 7, in which
the heart rate agreement statistic of the particular ECG signal segment is computed by adding the calculated differences of the heart rate value of the particular ECG signal segment from heart rate values of others of the ECG signal segments.

9. The medium of claim 7, in which when the one or more programs are executed by the at least one processor, the operations further comprise:
- identifying QRS complexes in the ECG signals;
- measure width values of the QRS complexes; and
- determine a final width value from the measured width values of the QRS complexes of the ECG signal segment received from the first channel, and in which the determination of whether or not the shock criterion is met is made also from the final width value.

10. The medium of claim 7, in which when the one or more programs are executed by the at least one processor, the operations further comprise:
- determining a final heart rate value from the measured heart rate value of the ECG signal segment received from the first channel, and
- in which the determination of whether or not the shock criterion is met is made also from the final heart rate value.

11. The medium of claim 7, in which
- the determination of whether or not the shock criterion is met is made from an ECG signal segment received from the first channel but not from an ECG signal segment received from the second channel.

12. A method for a wearable cardioverter defibrillator (WCD) system, the WCD system including an energy storage module configured to store an electrical charge, electrodes, a support structure configured to be worn by an ambulatory patient so as to maintain at least some of the electrodes on a body of the ambulatory patient, at least two distinct channels being defined by distinct respective pairs of at least some of the electrodes, a measurement circuit configured to sense two electrocardiogram (ECG) signals of the patient from the two channels respectively and to render values therefrom, and a processor, the method comprising:
- receiving the values of the ECG signals,
- isolating segments of the received ECG signals,
- measuring heart rate values of the ECG signal segments,
- calculating differences of the heart rate values among themselves,
- computing heart rate agreement statistics of the ECG signal segments, the heart rate agreement statistic of a particular one of the ECG signal segments computed from the calculated differences of the heart rate value of the particular ECG signal segment from heart rate values of others of the ECG signal segments,
- determining that the heart rate agreement statistic of a first one of the ECG signal segments that was sensed from a first one of the channels, is larger than the heart rate agreement statistic of a second one of the ECG signal segments that was sensed from a second one of the channels,
- and responsive to the heart rate determining, determining whether or not a shock criterion is met, the determination made from an ECG signal segment received from the first channel preferentially than from an ECG signal segment received from the second channel, and
- cause, responsive to the shock criterion being met, at least some of the stored electrical charge to be discharged via at least one of the electrodes through the ambulatory patient so as to deliver a shock to the ambulatory patient.

13. The method of claim 12, in which
the heart rate agreement statistic of the particular ECG signal segment is computed by adding the calculated differences of the heart rate value of the particular ECG signal segment from heart rate values of others of the ECG signal segments.

14. The method of claim 12, further comprising:
- identifying QRS complexes in the ECG signals;
- measure width values of the QRS complexes; and
- determine a final width value from the measured width values of the QRS complexes of the ECG signal segment received from the first channel, and
- in which the determination of whether or not the shock criterion is met is made also from the final width value.

15. The method of claim 12, further comprising:
- determining a final heart rate value from the measured heart rate value of the ECG signal segment received from the first channel, and
- in which the determination of whether or not the shock criterion is met is made also from the final heart rate value.

16. The method of claim 12, in which
the determination of whether or not the shock criterion is met is made from an ECG signal segment received from the first channel but not from an ECG signal segment received from the second channel.

* * * * *